(12) United States Patent
Bayat

(10) Patent No.: US 7,727,177 B2
(45) Date of Patent: Jun. 1, 2010

(54) FOUR FUNCTION SURGICAL INSTRUMENT

(75) Inventor: Ardeshir Bayat, Manchester (GB)

(73) Assignee: Inasurgica, LLC, Los Angeles, CA (US)

( * ) Notice: Subject to any disclaimer, the term of this patent is extended or adjusted under 35 U.S.C. 154(b) by 0 days.

(21) Appl. No.: 12/020,560

(22) Filed: Jan. 27, 2008

(65) Prior Publication Data

US 2009/0030414 A1    Jan. 29, 2009

Related U.S. Application Data

(63) Continuation-in-part of application No. 11/471,067, filed on Jun. 20, 2006.

(60) Provisional application No. 60/692,479, filed on Jun. 21, 2005.

(51) Int. Cl.
*A61N 1/30*   (2006.01)
*A61B 18/18*   (2006.01)

(52) U.S. Cl. .......................... 604/19; 606/51
(58) Field of Classification Search ............ 604/19
See application file for complete search history.

(56) References Cited

U.S. PATENT DOCUMENTS

| | | | |
|---|---|---|---|
| 4,492,231 A * | 1/1985 | Auth | 606/42 |
| 4,567,890 A | 2/1986 | Ohta et al. | |
| 4,950,281 A | 8/1990 | Kirsch et al. | |
| 5,151,102 A | 9/1992 | Kamiyama et al. | |
| 5,830,231 A * | 11/1998 | Geiges, Jr. | 606/205 |
| 6,527,745 B1 | 3/2003 | Kanda et al. | |
| 6,609,322 B1 | 8/2003 | Michelson | |
| 6,815,641 B2 | 11/2004 | Doherty | |
| 6,926,676 B2 | 8/2005 | Turturro et al. | |
| 6,928,764 B2 | 8/2005 | Freed | |
| 7,131,557 B2 | 11/2006 | Zimmerman et al. | |

FOREIGN PATENT DOCUMENTS

GB    2367751 A  *  4/2002

OTHER PUBLICATIONS

Kinall, A., Detailed Action, Oct. 24, 2008, Alexandria, Va., USA.
Bayat, A., A Novel, Triple-Function Vessel Dilator, Plastic and Reconstructive Surgery, Jan. 2003, vol. 111(1), pp. 501-502 (American Society of Plastic Surgeons).
Bayat, A.,et al., A Novel Irrigating Vessel Dilator for Microsurgery, plastic and Reconstructive Surgery, Sep. 2001, vol. 108(3), pp. 798-799 (Am. Soc. of Plastic Surg.).
King T. et al., Self Irrigating bipolar diathermy forceps: Technical note, Journal Neurosurgery, 1972, 37:246.

* cited by examiner

*Primary Examiner*—Nicholas D Lucchesi
*Assistant Examiner*—Jason Flick
(74) *Attorney, Agent, or Firm*—Cislo & Thomas, LLP

(57) ABSTRACT

A unique four function surgical instrument that performs aspiration, irrigation, dilation and cauterization with an innovative trigger mechanism. An embodiment is "gun-like" in configuration having a housing with a depending handle and a protruding trigger, a forward extending pair of forceps-like arms that terminate in dilation/cauterization tips and a common conduit between the forceps-like arms. The unique trigger mechanism utilizes a pinch valve concept where the trigger button has an elongated portion that has two slide surfaces with offset a recesses that act like tracks on which pinch sliders follow and the pinch sliders act like valve stems that squeeze close and allow to open silicone tubing. The end result, being a single poll, two stage actuator such that a half a pump of the trigger delivers irrigation or aspiration and a full pump delivers the other. The instrument provides the advantages of small size, ergonomical and all-in-one so as to eliminate the need for a surgeon to fumble around in switching between instruments.

19 Claims, 8 Drawing Sheets

FOUR FUNCTION SURGICAL INSTRUMENT

CROSS-REFERENCE TO RELATED APPLICATIONS

This application is a continuation-in-part of application assigned Ser. No. 11/471,067 that was filed Jun. 20, 2006 and the benefit this earlier filed application is claimed. Said earlier filed application in turn claims the benefit of a provisional application assigned Ser. No. 60/692,479 which was filed Jun. 21, 2005.

BACKGROUND OF THE INVENTION

1. Field of the Invention

This invention is in the field of surgical instruments and more particularly in the field of vessel dilators.

2. Related Art

A leading cause of mortality and morbidity of surgical patients is hospital borne disease transmission between patients. There are many machines and procedures for sterilizing and cleaning surgical instruments, including autoclaving. Despite the severity and rigor of these machines and procedures, the cleaning of the instruments is less than optimal. Specifically, blood denatures and hardens in crevices or embeds onto restricted areas of an instrument such that there are deposits of blood that remain after cleaning. These deposits of blood that remain after cleaning contain live pathogens. The result being that there is a risk of the transmission of disease from patient to patient.

It is theorized that humankind will never be able to devise a machine and/or process that in an economical and practical manner will optimally clean surgical instrument. Accordingly, it would be desirable to have surgical instrument that are disposable without compromising the efficacy and the cost effectiveness of performing surgery.

One type of surgical instrument is a vessel dilator. As the name implies, a vessel dilator provides intra-luminal vessel dilation during surgery. Vessel dilators are frequently used during surgical procedures as aid in fine dissection and vessel anastomosis. A conventional vessel dilator can be conceptualized as a modified forceps having elongated parallel tips which are highly polished. The parallel tips are pressed together to provide a single tapered shaft. The tapered shaft is inserted into a vessel and the parallel tips are allowed to separate thereby dilating the vessel. As a vessel dilator is inserted into a vessel, the dilator helps to hold the vessel wall and to avoid suturing the back wall to the front wall of the vessel.

Another type of surgical instrument is an irrigation instrument. Often, when a vessel is to be sutured, the vessel must be irrigated using an irrigation instrument. Irrigation is used to prevent drying of tissue, to remove tissue debris and blood, to keep vessel ends open and prevent floating adventitia at vessel ends interrupting satisfactory microvascular suturing and anastomosis. Irrigation keeps the operative field clean and inhibits blood clotting inside the lumen of the blood vessel.

Another type of surgical instrument is a suction instrument. Suction keeps the operative field clean and inhibits blood clotting inside the lumen of the blood vessel.

Another type of surgical devise is a cauterization instrument. Cauterization seals vessels and arrest bleeding. One conventional cauterization instrument is a bipolar-type blood vessel coagulation/stanching devise. Such a conventional devise employs a spark gap methodology using high-frequency current ranging between 0.5 to 3 MHz. This bipolar type devise has two electrodes (active and inactive electrodes) which are provided at both ends of a pair of forceps that are held by hand. Electric current flows only through the living tissue held between the ends of the forceps. Since electric current to a patient is applied only to a limited portion to be coagulated, bleeding from a blood vessel can be stopped completely without injuring other tissues. More specifically, the cauterization effect of the devise is obtained by coagulating the blood vessel using localized heating caused by the high-frequency current flowing through the living tissue.

Another surgical procedure of relevance here is anastomosis. Anastomosis covers a variety of procedures in which blood vessels (or other tubular members) are joined or reconnected. Vessels may be joined in a variety of relative orientations, including end-to-side and end-to-end. Anastomosis is traditionally performed by suturing the vessels together at the juncture between them. Alternatives to suturing have been developed, in order to prevent thrombosis which tends to occur at the points of penetration of the sutures. One such alternative, particularly for larger vessels, involves mechanical connectors such as collars. A second alternative is the use of surgical clips which are applied along the vessel juncture to perform a holding function similar to that of sutures, without penetrating the vessel walls.

A surgeon alternates amongst dilation, irrigation, suction and cauterization, during vessel dissection and anastomosis, using separate dilation, suction, irrigation and cauterization instruments. The act of switching among these four instruments is time-consuming and can interrupt the surgeon's attention and concentration.

In Bayat, A., A Novel, Triple-Function Vessel Dilator, Plastic And Reconstructive Surgery, January, 2003, volume 111 (1), pp. 501-502 (American Society of Plastic Surgeons) and in Bayat, A. et al., A Novel Irrigating Vessel Dilator for Microsurgery, Plastic and Reconstructive Surgery, September, 2001, Vol 108(3), pp. 798-799, Applicant herein invented a three functional vessel dilator performing the functions of dilation, irrigation and suction during vessel dissection and anastomosis. Still, when suturing a blood vessel or otherwise performing operative tasks, a surgeon must alternate between this three functional vessel dilator and a cauterization instrument. Alternating between these two instruments is time consuming and interrupts the surgeon's attention.

In patent application Ser. No. 11/471,067 upon which this application is a continuation-in-part and which is incorporated herein by reference as further referred to herein below, there is taught the ingenuity of a four function microsurgical instrument performing the functions of aspiration, irrigation, dilation and cauterization in a novel and unobvious design. Referring to FIG. 1 of application Ser. No. 11/471,067, the instrument has a body with forceps-like arms. A plunger valve extends perpendicular from the body in a direction away from a side region and is positioned for actuation by a user (see, FIG. 1, reference numerals 12 and 30). This ingenuous design advanced the art; but, there were stell needs for an instrument with even more enhanced ergonomics, better stability, ease of use and use which did require repositioning of a user's finger from gripping a forceps-like arm to contacting a plunger valve so at to actuate the valve.

Accordingly, there exists a need for an all-in-one, simple to use, easy to handle, lightweight, atraumatic macrosurgery and/or microsurgical instrument that improves the overall efficiency of operative procedures. There exists a need for a surgical instrument configured so that all the four functions of dilation, suction, irrigation and cauterization fit together in one instrument and enabling a surgeon to perform operative tasks without having to switch instruments. There is therefore a need for a four function vessel dilator performing the functions of dilation, irrigation, suction and cauterization for use, including, during vessel dissection and anastomosis. There exists a need for an instrument for microsurgery that provides the advantages of being small in size, being ergonomical, being all-in-one, eliminating the need for a surgeon to fumble around in switching between instruments, reducing time consumption and reducing frustration.

There exists a need for a surgical instrument possessing the functions of dilation, irrigation, aspiration and cauterization where the user is NOT required to reposition and move the user's finger from gripping a forceps-like arm to the finger contact area of an actuation means for controlling irrigation-fluid and aspiration-suction.

There exists a further need for a surgical instrument possessing the functions of dilation, irrigation, aspiration and cauterization where the mechanism for controlling irrigation-fluid and aspiration-suction occupies a small and minimized volume such that it is containable in an instrument for microsurgery.

There exists a further need for a surgical instrument possessing a valve that has a high level of ergonomics; in particular, there would be a biometrically comfortable force to actuate the valve, a short travel distance for actuation, non-awkward finger positioning and a high level of instrument support within the hand.

There is a need for a totally disposable instrument that is low in cost and avoids the transmission of pathogenic agents, because current sterilization techniques are not totally fail-safe.

The present invention satisfies these needs, as well as others, and generally overcomes the presently known deficiencies in the art.

SUMMARY OF THE INVENTION

The present invention is directed to a novel and innovative surgical instrument possessing the four functions of vessel dilation, irrigation, aspiration and cauterization in a unique configuration. The instrument can have a unique and innovative trigger mechanism that is a single poll, two stage actuator such that a half a pump of the trigger delivers irrigation or aspiration and a full pump delivers the other.

An object of the present invention is the combined functions of vessel dilation, irrigation, aspiration and cauterization into a single instrument. An interrelated object is easier use, less mistakes and reduced fatigue compared to the use of separate instruments.

An object of the present invention is a single actuator for controlling both irrigation fluid and aspiration suction. Interrelated is the objective of a single pole mechanism that controls both irrigation and suction.

An object of the present invention is an instrument that can easily be manipulated in a controllable fashion.

An object of the present invention is an instrument that is comfortable to use. An interrelated object is an instrument where fingers are deployed in natural positions and especially where fingers are deployed with a natural curl. An interrelated object of the present invention is an instrument that fits comfortably in the palm of user's hand between the first joints of the user's index and middle fingers and the fleshy portion underneath the user's thumb known as the thenar eminence.

One aspect of the present invention is a unique and innovative surgical instrument possessing the four functions of vessel dilation, irrigation, aspiration and cauterization. The surgical instrument has a housing component which is comprised of three subcomponents. The first subcomponent is a body portion having a longitudinal axis so as to define forward and posterior directions. The second subcomponent is a handle portion that extends downward from the body portion. The third subcomponent is a butt that extends from the body portion in the posterior direction.

There are a pair of oppositely opposed forceps-like arms that extend in the forward direction from the body portion. They are resiliently mounted to the body portion and insulative with each forceps-like arm having a distal end. At each distal end of each of the forceps-like arms, there is a dilation tip that is electrically conducting and communicable with electrical power.

A common conduit extends in the forward direction from the body portion. It delivers irrigation-fluid and aspiration-suction in proximity to the dilation tips. There is a trigger button means mounted to the housing that is positioned for actuation by the user. The trigger button means is in communication with a triggered controlled irrigation-fluid and aspiration-suction transmission system which is in fluid communication with the common conduit.

This aspect of the present invention can be qualitatively conceptualized as having a gun-like configurations or "T"-like configuration. Alternatively, it can be qualitatively conceptualized as having a handle with front forceps-like arms that are balanced by a posterior butt.

Another aspect of the present invention is a unique and innovative triggered controlled irrigation-fluid and aspiration-suction transmission system for a novel surgical instrument. This mechanism has a trigger which has a forward portion and a posterior portion. The posterior portion has a first elongated slide surface which has a first recess. The posterior portion also has a second elongated slide surface that is substantially parallel to the first elongated slide surface and which has a second recess where said second recess is posterior relative to the first recess. The trigger displaces in the posterior direction. There is a means for biasing the trigger forward.

There is first a pinch slider that has a first pinch surface and an oppositely opposed first ride surface. The first ride surface rides on the first elongated slide surface of the posterior portion of the trigger. There is a second pinch slider that has a second pinch surface and an oppositely opposed second ride surface. This second ride surface rides on the second elongated slide surface of the posterior portion of the trigger. Both pinch sliders move back and forth as the trigger is displaced in the posterior direction.

Opposed to the first pinch surface and spaced apart a distance there from is a first pinching back surface. This first pinching back surface is spaced apart a distance from the first pinch surface such that a tube can be seated between the first pinching surface and the first pinching back surface such that the tube will have a substantially open lumen when the first ride surface rides in the first recess and has a pinched closed lumen when the first ride surface rides otherwise on the first elongated slide surface.

Opposed to the second pinch surface and spaced a distance apart there from is a second pinching back surface. This second pinching back surface is spaced apart a distance from the second pinch surface such that a tube pan be seated between the second pinch surface and the second pinching back surface such that the tube has a substantially open lumen when the second ride surface rides in the second recess and has a pinched closed lumen when the second ride surface rides otherwise on the second elongated slide surface.

This aspect of the invention can be qualitatively conceptualized as comprised of a trigger button with an elongated portion that has recesses and acts like a track. The pinch sliders act like valve stems that follow on the recesses. The pinch sliders press against silicone tubing so as to squeeze close and open the silicone tubing. The end result, including, being a single poll, two stage actuator.

The present invention has many advantages which include the following. The present invention has the advantages of being ergonomical and light weight whereby it sits well in a user's hand, reduces fatigue, facilitates fluid and accurate movements, facilitates ease of use and enhances control. The instrument has the advantage of eliminating the need for a surgeon to use multiple instruments and commensurately, the number of assistance to a surgeon. Overall, the instrument has the advantage of reduces operating time and concomitantly, reducing operating error, the amount of anesthesia and cost. The entire instrument is sufficiently inexpensive to be totally disposable. This is paramount to safety for the cleaning of surgical instrument is usually suboptimal with blood getting stuck on the instrument, after cleaning.

BRIEF DESCRIPTION OF THE DRAWINGS

These and other features, aspects and advantages of the present invention will become better understood with reference to the following description, appended claims and accompanying drawings where:

DETAILED DESCRIPTION OF THE INVENTION

The invention is a unique and innovative all-in-one four function microsurgical instrument with a unique trigger design which performs the functions of aspiration, irrigation, dilation and cauterization. The instrument is ergonomical and user friendly whereby it can be sized for being a microinstrument designed for work with say vessels having a diameter of about one or about two millimeters. The instrument can also be sized for being a macro-instrument designed for work with say intestines.

Overview of the Housing

Figure 1:
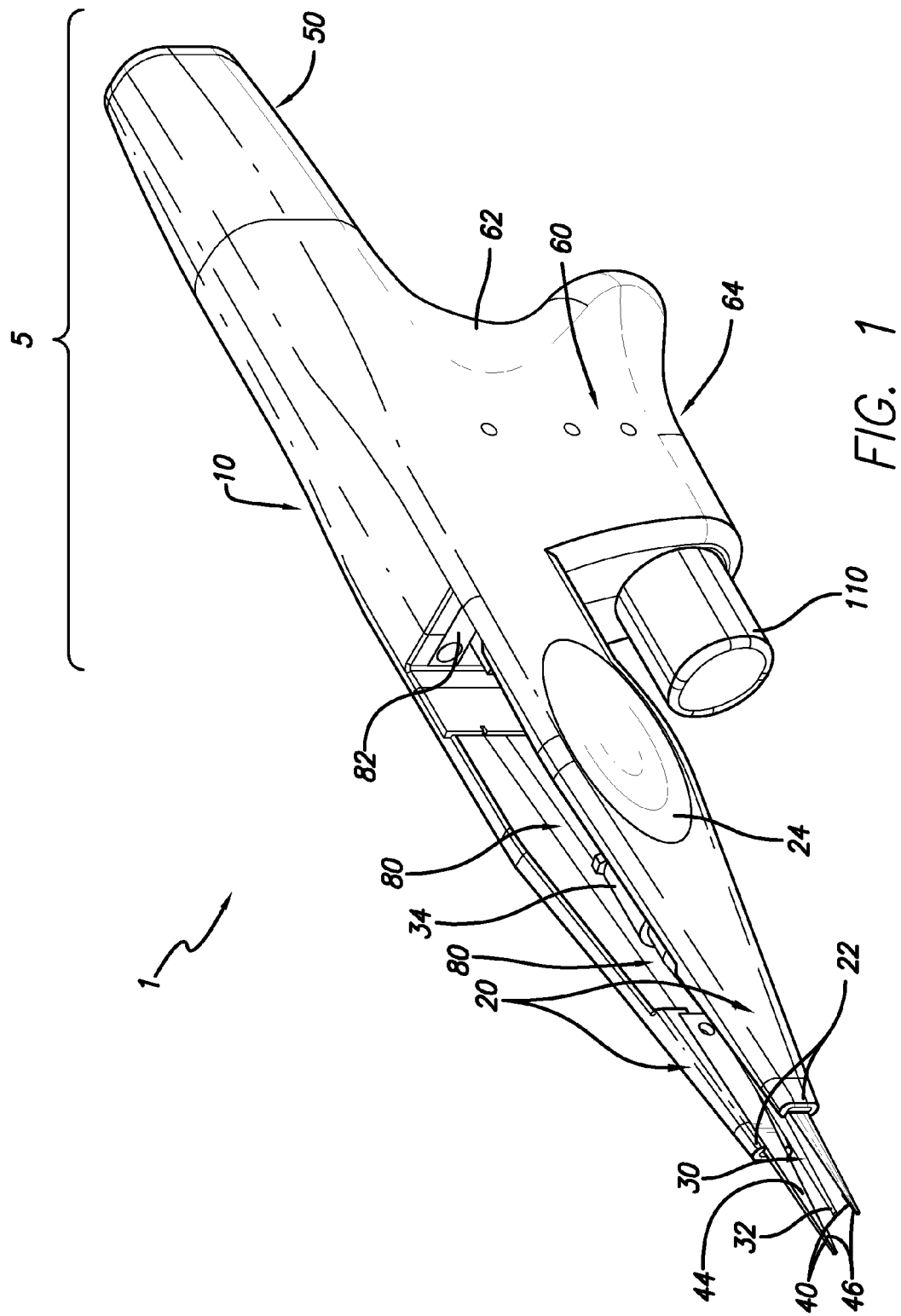
FIG. 1 is a perspective view of the exterior of an embodiment of the present invention looking onto a left side.

Referring to FIG. 1, the surgical instrument (1) of this invention has a housing (5). This housing (5) is comprised of body portion (10), handle portion (60) and butt portion (50). As discussed further herein below, typically, this housing (5) if of an industrial design such that it is integral with forceps-like arms (20, see, infra.) and is that is manufactured as a right tray and left cover which are pressed or fastened together.

Body Portion

Referring to FIG. 1, the body portion (10) has a longitudinal axis so as to define forward and posterior directions, a pair of oppositely opposed lateral sides, front side and an upper side. If the handle portion (60) is narrower than the body portion (10), the body portion can have a lower side (see, discussion, infra.)

Handle Portion

Figure 10:
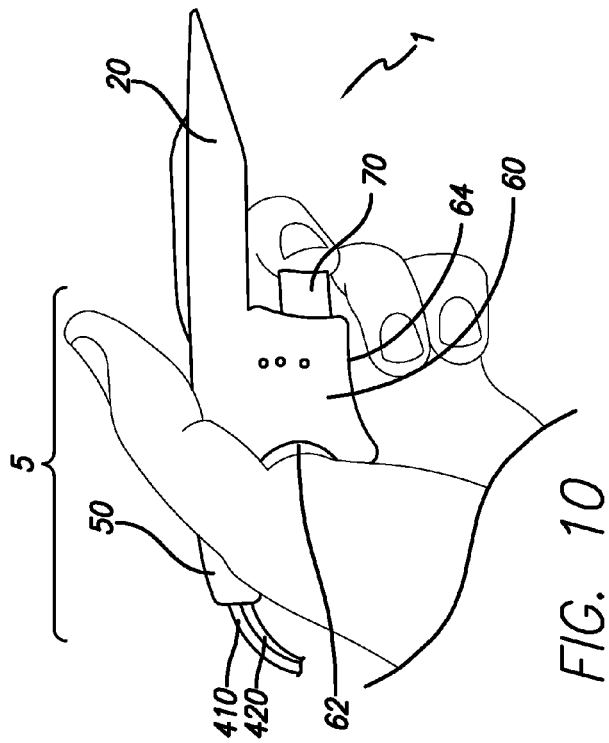
FIGS. 9A and 9B are graphs plotting force to displace a trigger verses displacement and FIG. 10 is a perspective which shows an embodiment of the present invention held in an user's hand.

Referring to FIG. 1, the handle portion (60) depends (loosely meaning extends downward when the instrument is in a horizontally prone position) from the body portion (10) so as to define a lower direction. The can depend perpendicular or at a angle, with perpendicular being preferred. Referring to FIG. 10, the handle portion has oppositely opposed lateral sides, a forward side, a lower side and a posterior side. The handle portion (60) has a width and length that is suitable for grasping in the area of a user's palm between about thenar eminence and about the first joints of the user's first finger (thumb) and second (index) finger.

Figure 7:
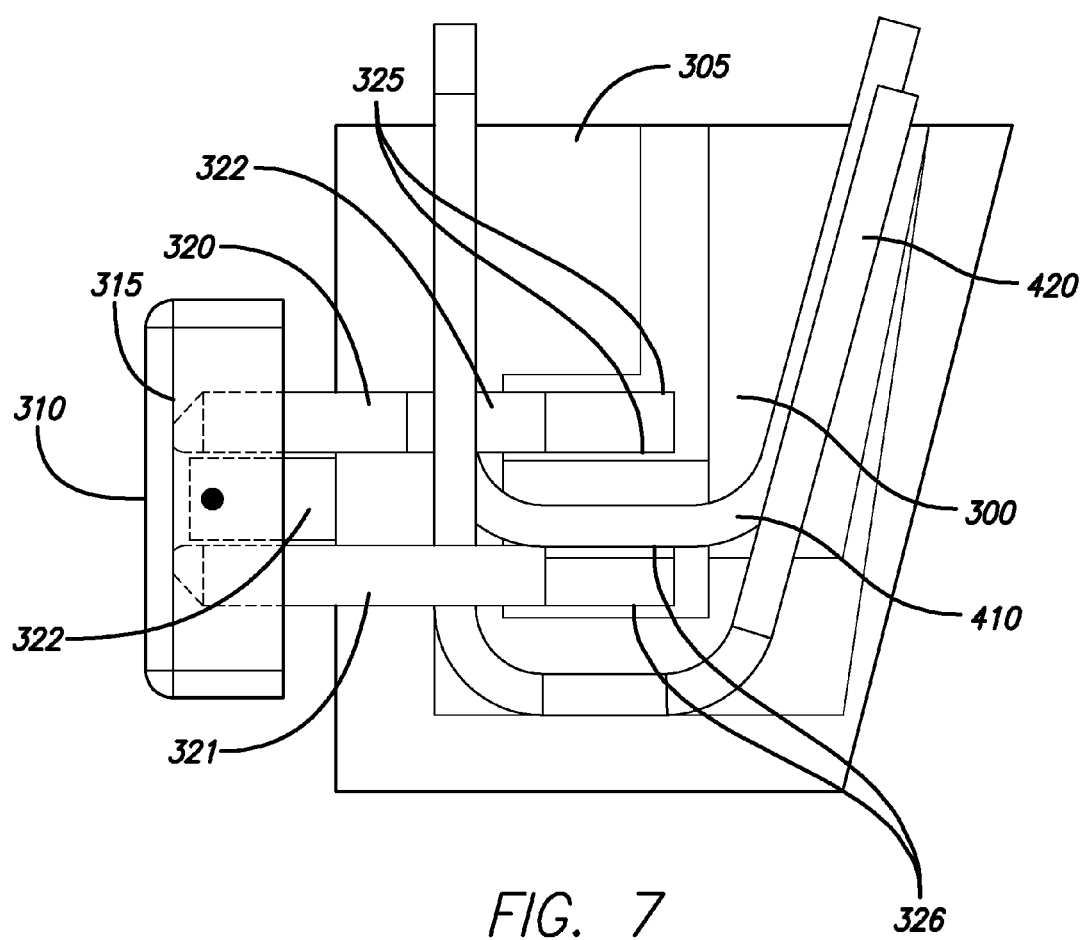
FIG. 7 is a side view that shows a triggered controlled irrigation-fluid and aspiration-suction transmission system according to the present invention.

Referring to FIG. 10, preferably, the width of the handle portion (60) is sized such that when posterior arcuate (62, see, infra) of the handle potion (60) buttresses against the thenar eminence of a user's hand, the third (middle) finger of the user's hand naturally curls and rests on the finger contact surface or surfaces of a trigger button means (110, 210, 310). Preferably, the handle portion (60) extends in the lower direction sufficiently for stable support of the instrument (1) by the user. Referring to FIGS. 1 and 7, in embodiments of the invention having a single or dual plunger-like trigger button means (110, 310), most preferably, the length of the handle portion (60) is long enough such that the finger contact surface or surfaces of the trigger button means (110, 210, 310) aligns with the third (middle) finger and is not so long that the bottom of it contacts with or interferes with the a user curling the user's fourth (ring) finger and fifth (pinkie) finger.

Referring to FIG. 1, the handle portion (60) has a posterior arcuate (62). Referring to FIG. 10, this posterior arcuate (62) sits in the first web space of an user's hand and is appropriately sized to fit in that webspace. Preferably, the radius of curvature of the posterior arcuate (62) is not so small at to pinch the thenar eminence. Preferably, the radius of curvature of the posterior arcuate (62) is not so great such that there are gaps or spaces between the arcuate surface and the thenar eminence. In an embodiment of the invention, using straight line approximations, the arcuate surface would fit into the rays of an about 75 degree to an about 88 degree angle. Accordingly, the posterior arcuate (62) forms a saddle to sit in the first web space of user's hand and rests against thenar eminence of the user's hand.

Referring to FIGS. 1 and 10, the lower surface of the handle portion (60) can be arcuate (64) to accommodate the user's fourth or fifth finger which may be at least partially extended or curled below the lower surface of the handle portion (60). The forward side of the handle portion (60) is typically linear and can slightly angle in the posterior direction so the user's middle finger naturally curls onto the finger contact surface of a trigger button means (115, 215, 216, 315).

Butt Portion

Referring to FIG. 1, there is a butt portion (50) that extends posterior from the body portion (10) about along the longitudinal axis of the body portion (10). In alternative embodiments, the butt portion (50) can be at a modest angle relative to the longitudinal axis. Referring to FIG. 10, typically, there is an upper side, oppositely opposed lateral sides, a posterior side and a lower side. Preferably, the lower side is restable on and extends over at least a portion first dorsal web space of a user's hand.

Figure 2:
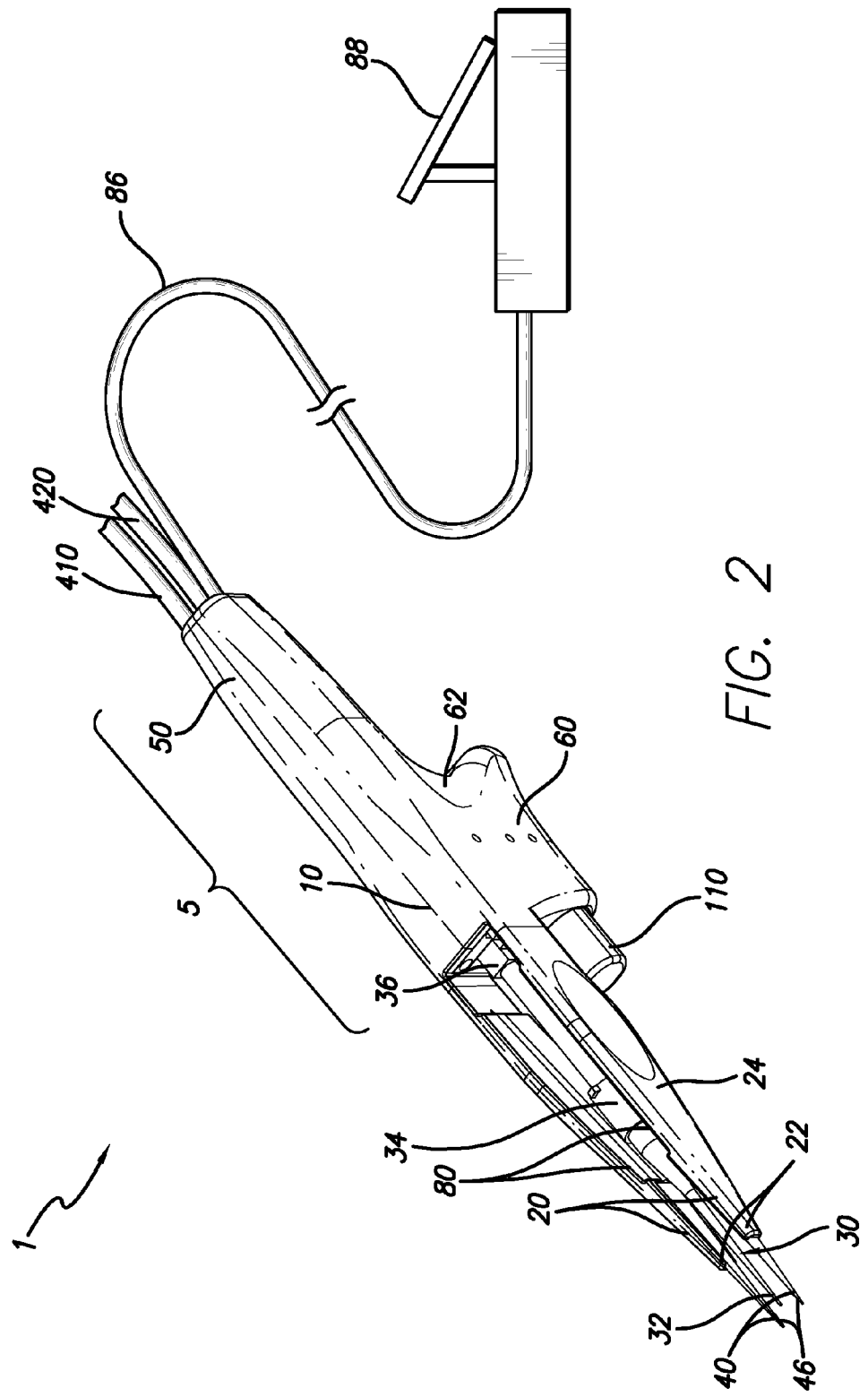
FIG. 2 is a perspective view of the exterior of an embodiment of the present invention looking down onto a top side.

In alternative embodiments, the extension of the butt portion (50) can be very minimal down to a negligible posterior side of the body portion (10). Referring to FIG. 2, preferably, the length of the butt portion (50) makes the instrument (1) balanced; that is, it functions, including, as a counterweight to the forceps-like arms (20). Preferably, the length of the butt portion (50) should not be too long so as to make the instrument (1) to heavy. Referring to FIG. 10, preferably, the length of the butt portion (50) should not be too short such that the instrument does not rest comfortably over the first dorsal web space of the user's hand so as to provide stability.

Referring to FIG. 2, there is one or more openings (52) in back of the butt portion (50) that are sized to run out two tubes (410, 420) and a wire (86). In alternative embodiments, this opening (52) or these openings (52) are on the top side of the butt portion (50) or at other points elsewhere about the housing (5). The out-routing of these two tubes (410, 420) is further discussed below.

Forceps-Like Arms

Referring to FIG. 1, there are a pair of oppositely opposed forceps-like arms (20) that extend forward from the body portion (10) on or approximately along the longitudinal axis of the body portion (10). In alternative embodiments, the forceps-like arms (20) can be at a modest angle relative to the longitudinal axis. Each of the forceps-like arms (20) has a distal end (22). Extending past the distal ends (22) are dilation tips (40, see, infra.)

The forceps like arms (20) extend in substantially parallel fashion from the body portion (10). Typically, the forceps-like arms (20) taper gradually to a narrow breadth as distance increases from the body portion (10).

The forceps-like arms (20) are insulative (preferably, non-conducting.) Referring to FIG. 10 and as explained further below, a user's first finger (thumb) and second (index) finger contact the forceps-like arms (20). Insulative means that at least the intended finger contact area for one of the user's fingers is non-conducting. Preferably, the entire forceps-like arm (20) is non-conducting. In embodiments of the invention, non-conducting does not mean a particularly high resistance that no current at all flows and means that a user is not distracted, annoyed or harmed by any current that might flow. Insulative to the degree of being non-conducting is preferred.

The forceps-like arms (20) are resiliently mounted to the body. Referring to FIG. 2, typically, the forceps-like arms (20) are integral with the housing. In such a configuration, resilient means that in a resting state of the instrument, the forceps-like arm (20) are spread apart and capable of deforming when squeezed so as to bring together the dilation tips (40) and thereafter return to about a resting state of being about spread apart.

The forceps-like arms (20) can be a separate structure that is hinge mounted to the body portion (10) or mounted by way of a docking station (see, discussion below on a modular instrument.) In a hinged configuration, resilient mounting is accomplished by way of a torsion spring or a compression spring on the inside of the hinged joint or an elastic band or spring running over the outside of the hinged joint.

Optionally, there is a gripping pad (24) on the exterior of the forceps-like arms (20). The gripping pad (24) can be a widened area of the forceps like arms (20). In addition or alternatively, the gripping pad (20) can be a depression or recess. In addition or alternatively, the surface of the gripping pad (20) can have knobs, protrusions, striations and/or a grating. Preferably, the gripping pad (20) is positioned along the exterior of the forceps-like arms such that the tip of the user first finger (thumb) or second (index) finger rests on the gripping pad (20) in an anatomically natural position.

In another embodiment, the outer surfaces of the forceps-like arms (20) is provided with undulations which facilitates gripping. In another embodiment, there can be a thumb/finger tab that projects from a forceps-like arm (20) and is positioned to enhance gripping, control and the ergonomics of the instruments. This thumb/finger tab can further have an array of recesses, protrusions or nodulations to further enhance gripping.

Dilation Tips

Figure 3:
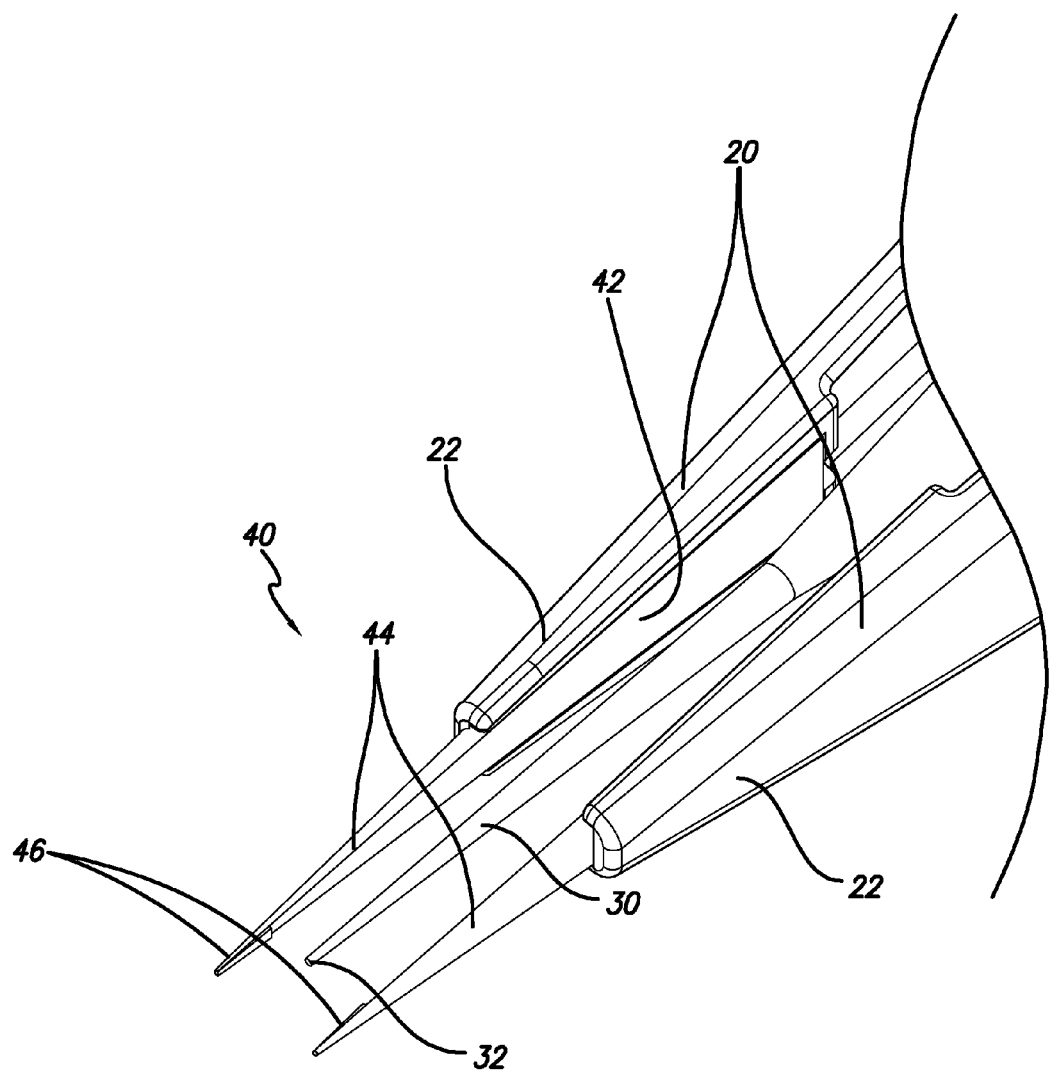
FIG. 3 is a perspective view of the exterior of forceps-like arms and dilation tips according to the present invention looking down onto a top side.

Referring to FIG. 3, there is a dilation tip (40) at each distal end of each of the forcep-like arms (20) that is electrical conducting and communicable with an electrical power source which preferably has actuation means for the electrical power. Typically, the dilation tip is an elongated metal bar that tapers to a point. Preferably, the metal is stainless steel of a fine enough grade to be shapeable into a tip, as previously described.

Figure 4:
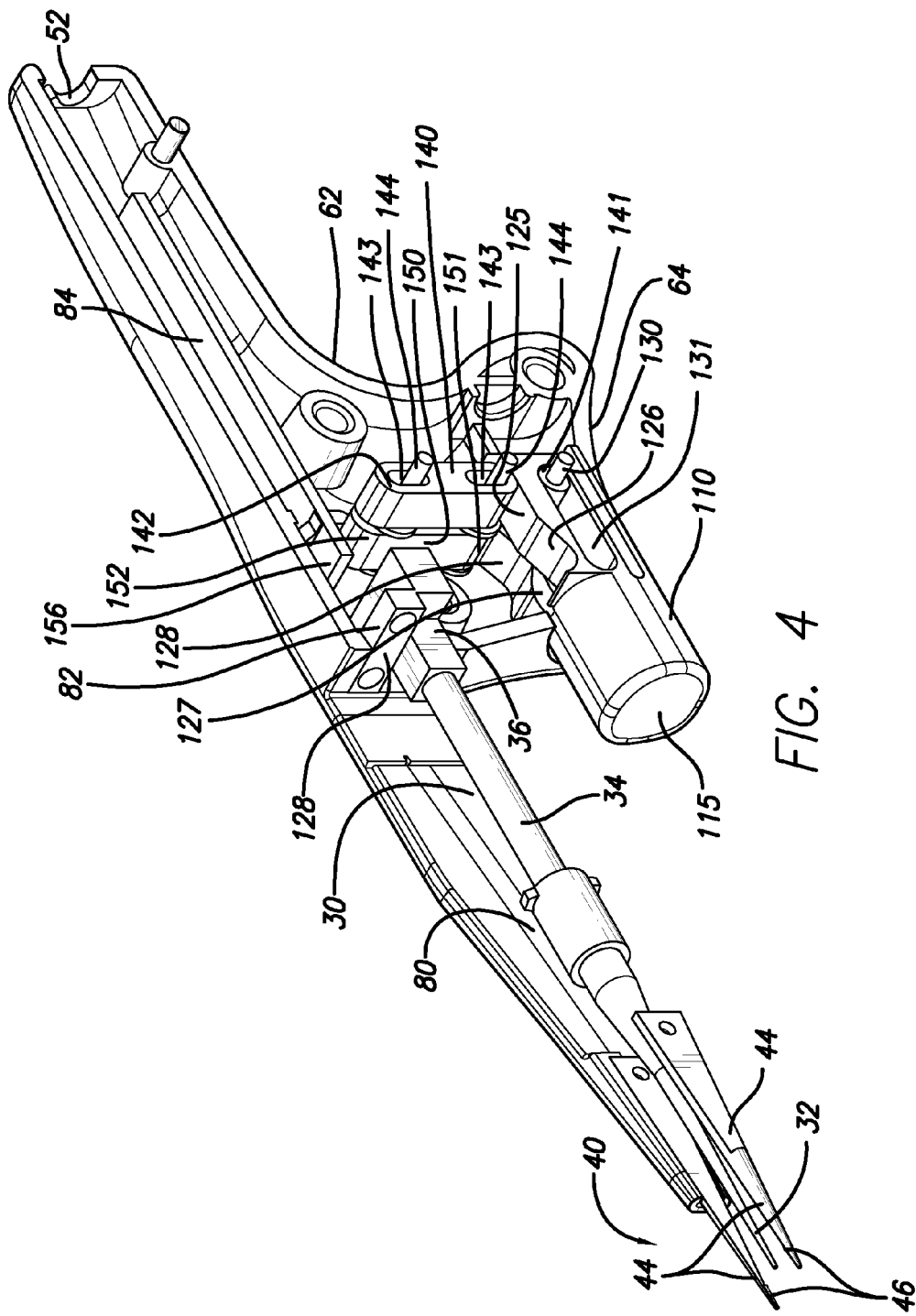
FIG. 4 is a perspective view of the interior of an embodiment of the present invention looking onto a left side.

Referring to FIGS. 3 and 4, typically, the dilation tip has a first length (42) and a second length (44). The first length 42) runs coextensively with the distal end of the forceps-like arm (20) and is embedded or otherwise affixed to the forceps-like arm (20). Preferably, this first length (42) has a narrower width then a second length (44) (discussed below.) Thus this first length is like a recess with a shoulder (at the point of the beginning of the second length (42) so as to facilitate attachment of the dilation tip (40) to the forceps-like arm (20).

There is a second length (44) of the dilation tip (40) that extends from the distal ends of the forceps-like arms (20). The second length of the dilation tip (44) can be configured for contacting a blood vessel and is approximately shaped like "b" rotated 90 degrees or sharpened/tapered to a point. The outer surface of this second length (44) can be flat or rounded.

Referring to FIG. 3, preferably, at the distal end of each of the dilation tips (20) on the inner sides of the second lengths (44) (that is, the sides that oppose each other on the dilation tips (40)) there is a ridge (46). These opposing ridges (46) perform the function of stops to spread the inner surfaces of the dilation tips (40) near the distal ends. The gap thereby created is utilized as room for a common conduit (30, see, infra.)

In another embodiment, there is a groove in the inner surface of the forceps-like arm (20) (that is, the surface that opposes the other forceps-like side arm (20).) The common conduit (30, see, infra.) is totally received in this groove so as allow the dilation tips to close together (40) in near perfect approximation. In another embodiment, the groove is dimensioned so that the common conduit (30) partially fits into a first forceps-like arm (20) and there is a groove in the inner surface of the second forceps-like arm (20) that mates with the common conduit (30) which is partially recessed in the first forceps-like arm (20). Thus, when the two forceps-like arms (20) are pressed together, this groove allows the dilation tips (40) on each of the forceps-like arms (20) to close with near perfect approximation.

Common Conduit

Referring to FIGS. 2 and 3, there is a common conduit (30) for the delivery irrigation-fluid and aspiration-suction in proximity to the dilation tips (40). The common conduit (30) extends forward from the body portion (10) about along the forceps-like arms (20). The common conduit (30) can be positioned between the opposing forceps-like arms (20). It can also be positioned to run along or inside a forceps-like arm (20) with a suitable exit port fixture to direct the flow of irrigation-fluid and aspiration suction. The common conduit

(30) can be positioned outside the pair forceps-like arms (20) with a suitable exit port fixture to direct the flow of irrigation-fluid and aspiration suction. Preferably, the common conduit (30) is centrally located between the forceps-like arms (30) such that when the forceps-like arms (20) are pressed together, the common conduit (30) is located immediately behind the dilation tips (40) mounted on the forceps-like arms (20).

The term common conduit (30) includes a single conduit, two separate conduits, co-axial conduits with two channels and side-by-side conduit strips where there are two conduits/channels with one delivering fluid and the other suction. Typically and preferably, the common conduit (30) is a single tube, channel or conduit. Preferably, the end of the common conduit (32) near the dilation tips tapers down to a needle like point.

Referring to FIG. 4, in an embodiment of the invention, there is a Y-connector block (36) which is a forward facing interface positioned on the front side of the body portion. Typically, the Y-connector is just below a two hole bridge (82) for running electrical wires. Preferably, the Y-Connector block is integral with the 2 hole bridge (82) and the 2 hole bridge (82) buttress against the upper side of the body portion (10).

Continuing to refer to FIG. 4, in this embodiment of the invention, there is a spar tube (34) is inserted into the Y-Connector block (36) and extends there from.

A pipette tip, needle or cannula (32) is attached to the spar tube (34) and forms the end of the common conduit (30). An example of a suitable plastic needle (32) is a standard mini Yankauer, which is conventionally used as a cannula in pediatric anesthetic catheters. The pipette tip, cannula or needle (32) are either fixedly or irremovable mounted to the spar tube (34). The pipette tip, needle or cannlula (32) is typically pushed onto the end of the spar tube (34). Friction between the inside surface of the pipette tip, needle or cannula (32) with the outside surface of the spar tube (34) is usually sufficient to hold the pipette tip, needle or cannula (32) in place. A nipple or sleeve can be used to join the pipette tip, needle or cannula (32) onto the end of the spar (34).

In an embodiment of the invention, there is a pipette tip, needle or cannula (32) attached to a central spar tube (34) which extends from a Y-connector block (36) positioned at about the front side the body portion (10).

Referring to FIG. 3, the common conduit (30) delivers irrigation-fluid and aspiration-suction in proximity to the dilation tips (40) and is in fluid communication with a triggered controlled irrigation-fluid and aspiration-suction transmission system (100, 200, 300). Proximity does not connote any particular distance and means an operative distance so as to deliver irrigating fluid, or when switched, aspiration/suction, in the area of the dilation tips (30). One millimeter or less is preferable. The function provided by the common conduit (30) is determined by an irrigation-fluid and aspiration-suction control and transmission system. When aspirating, the common conduit (30) can be used to extract fluid.

In a most preferred embodiment, the tip or end of common conduit (32) is set back to allow the dilation tips (40) of forceps-like arms (20) to close. As discussed herein, the dilation tips (40) can have opposing ridges (46.) The end of common conduit (32) approaches the start of the ridges (46). Thus, the ridges (46) provide room for the end of the common conduit (32) when the dilation tips (30) are pressed or squeezed together.

Triggered Controlled Irrigation-Fluid and Aspiration-Suction Transmission System Referring to FIGS. 4, 5, 6 and 7, there is a triggered controlled irrigation-fluid and aspiration-suction transmission system that is partially disposed in the housing that is in fluid communication with the common conduit (30) and sources for fluid and vacuum. It is partially disposed in housing for at least the reason that a trigger means extends out from the housing and there are tubes outside the housing. This system is comprised of a control system (100, 200, 300) and a transmission means (410, 420).

Control System Subcomponent

Figure 5:
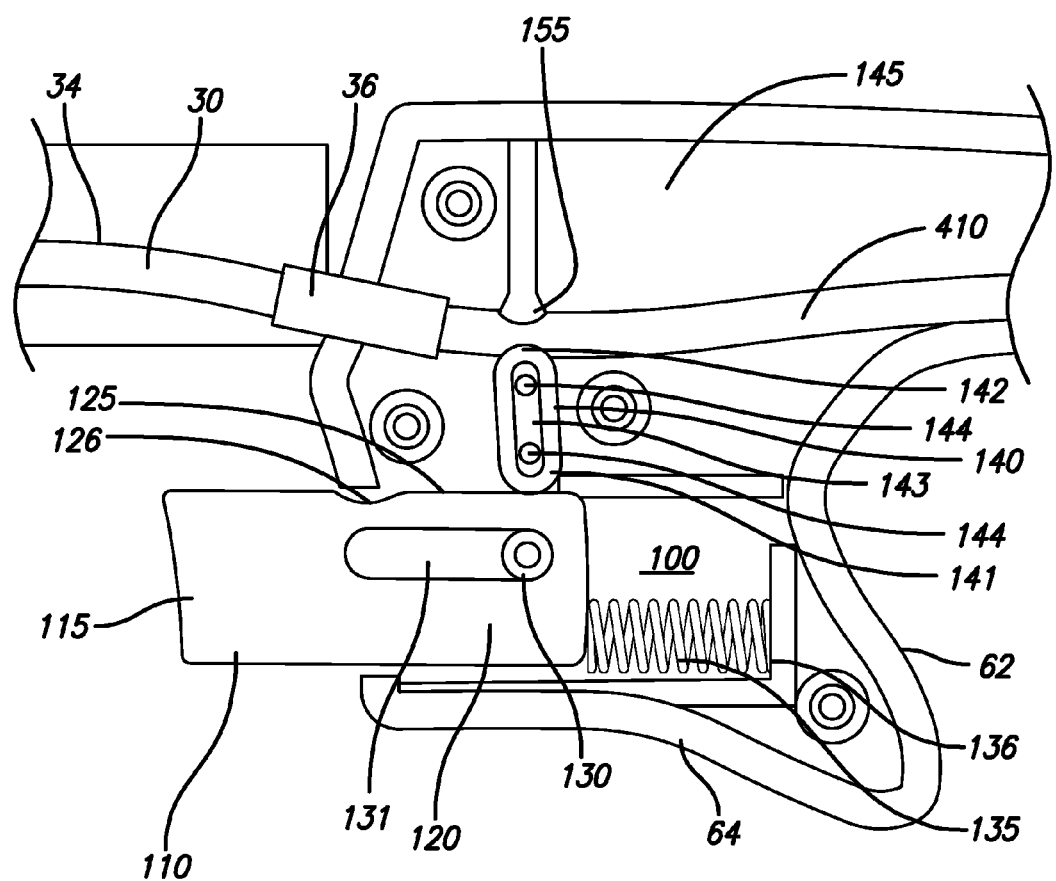
FIG. 5 is a perspective view of a triggered controlled irrigation-fluid and aspiration-suction transmission system according to the present invention.
Figure 6:
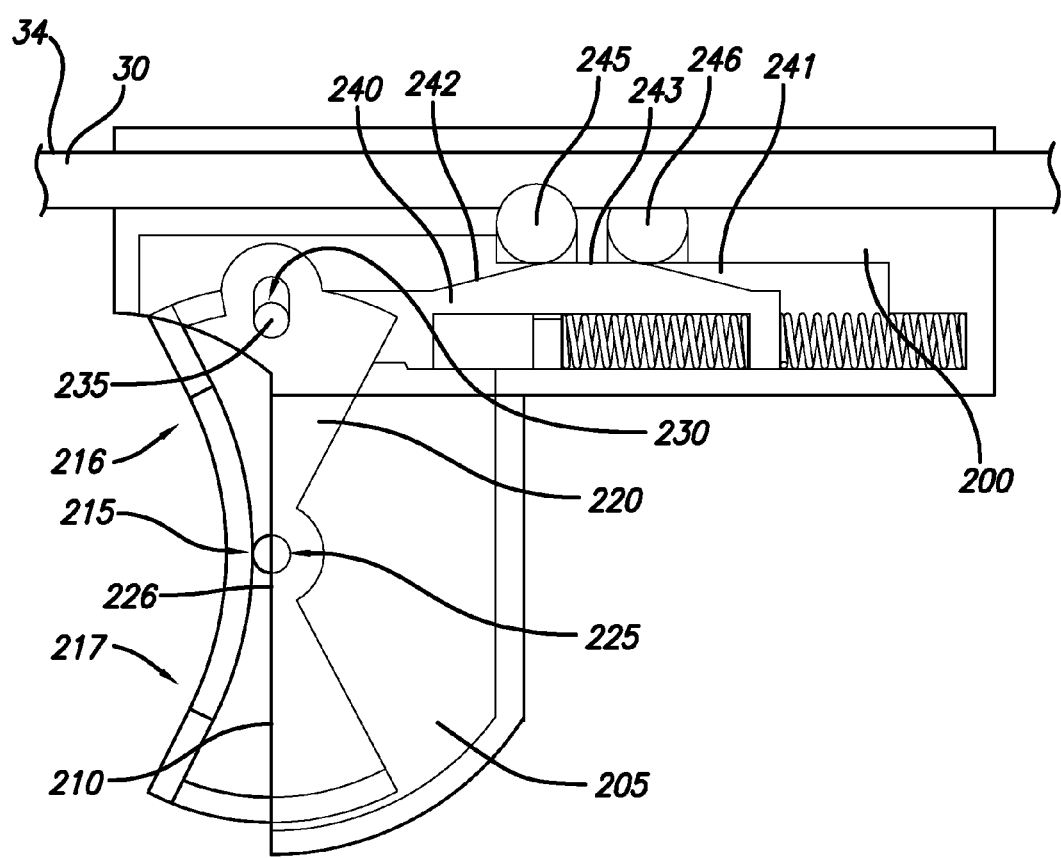
FIG. 6 which is a side view that shows a triggered controlled irrigation-fluid and aspiration-suction transmission system according to the present invention.

Referring to FIGS. 4, 5, 6 and 7, the control system has a trigger button means (110, 210, 310) mounted to the housing (5) that is positioned for actuation by the user and most preferably, mounted to the handle portion (60). The trigger button means (110) can have the structure of being a single plunger-like button (110) which travels a longitudinal distance as illustrated in FIG. 5. It can have the structure of a dual plunger-like button (310) which travels a longitudinal distance as illustrated in FIG. 7. It can have the structure of a rocker-like switch (210) as illustrated in FIG. 6. It can have other structures such as like a slide switch.

A single or dual plunger-like button (110, 310) which travel a longitudinal distance are preferred because, this facilitates actuation by a user with the user's third (middle) finger with relatively little or no repositioning of the user's third (middle) finger. This is in contrast to a rocker-like switch button (210) which requires relatively greater repositioning movement by the user of the user's third (middle) finger between the two finger contact surfaces of the rocker-like switch button (210). A single plunger-like button (110) which travels a longitudinal distance is most preferred because, it requires no repositioning of the user's third (middle) finger and therefore has enhanced ergonomics and simplicity of use.

Trigger force can be reduced by using materials with a lower coefficient of friction compared to other materials. This in turn enables the use of a softer spring (135). In embodiments of the present invention, the trigger force is at least great enough that the trigger is not inadvertently actuated when manipulating the instrument and/or facilitates gripping and holding of the instrument. In common parlance, the trigger does not feel "mushy."

Optionally, the finger contact surface of the trigger button (110, 210, 310) can be embellished with a ring-like or cage-like structure into which an operator inserts the users third (middle) finger. This optional feature promotes bipolar motion at the expense of ergonomics.

Optionally, the finger contact surface can have recesses or bumps to enhance finger gripping.

The triggered controlled irrigation-fluid and aspiration-suction transmission system that is partially disposed in the housing. As further discussed below, typically, the housing is designed and manufactured in two halves; that is, a right tray (105, 205, 305) and a left cover. The right tray has features that are utilized in or are apart of the control system (100, 200, 300).

Preferably, the control system employs a pinch valve concept is employed.

Referring to FIGS. 4 and 5, one embodiment of the control system (100) works off a trigger button means (110) that is a single button plunger-like trigger. There is a trigger button means (110) having a forward portion (115) that extends forward from the housing (5). This forward portion has a finger contact surface. There is a posterior portion (120) that is preferably disposed in the handle portion (60) of the housing (5). This posterior portion (120) is bar-like in shape and has a top surface with features as described below.

The trigger button means (110) is displaceable in the posterior direction. The trigger is slidably mounted to the housing (5) by way of a longitudinal elongated slot (131) in the posterior portion (120). This longitudinal elongated slot (131) is seated on roller post (130) that protrudes from the right tray (105).

There is a means for biasing (135) forward the trigger button means (110). This means can be a compression spring. The compression spring spans from the rear of the posterior portion (120) of the trigger button (110) to a shoulder (136) protruding from the right tray (105). It can be a torsion spring. It can be an elastic band or member. It can be an hydraulic or air cylinder. It can be a motor powered by electricity, pressurized hydraulic fluid or compressed air. A spring is preferred and a compression spring is most preferred. This means for biasing (135) is discussed further below.

The top surface of the posterior portion (120) of the trigger button means has a first elongated slide surface (125) that has a first recess (126) and acts like a track. There is a second elongated slide surface (127) in the top surface of the posterior portion (120) that is substantially parallel to the first elongated slide surface (125) and has a second recess (128), where said second recess (128) is posterior relative to the first recess. This second elongated slide surface and second recess also acts like a track.

There is a first pinch slider (140) and a second pinch slider (150). The pinch slider (140, 150) can be rectangular, square, round (called a pinch cylinder (245, 246) (see, below)) or other suitable shape. Each has a pinch surface (142, 152) and oppositely opposed ride surface (141, 151). In embodiments of the invention, the pinch sliders (140, 150) have two elongated slots (143) (slot not illustrated for second pinch slider) and are mounted on support posts (144) which protrude from the right tray. Preferably, the ride surface (141, 151) of each pinch slider (140, 140) is rounded to facilitate riding. Preferably, the pinch surface (142, 152) is a triangular-like to facilitate pinching. In the case of a cylindrical pinch slider (245, 246,) then the ride surface (141, 151) and pinch surface (142, 152) are continuous.

As mentioned, there is a first ride surface of the first pinch slider (140). This first ride surface (140) rides on the first elongated slide surface (125) of the trigger button means (110). The first pinch slider (140) acts like a valve stem and moves back and forth as the first recess (126) in first elongated slide surface (125) passes underneath it when the trigger button means (110) is displaced. That is, when the first recess (126) is underneath the first pinch slider (140), it can move into a lower position.

There is a first pinching back surface (155) that protrudes form the housing tray and is oppositely opposed to a first pinching surface (142) of the first pinch slider (140). This first pinching back surface (155) is spaced apart a distance from the first pinching back surface (155) such that a tube (410) can be seated, and preferably conformingly seated, between the first pinching back surface (155) and the first pinching back surface (142) with the tube (410) having a substantially open lumen when the first ride surface (141) rides in the first recess (126). The lumen of tube (410) is pinched closed when the first ride surface (141) rides otherwise on the first elongated slide surface (125). In operation, the first pinch surface (142) buttresses against a first silicone tube (410) and as it moves back and forth, it squeezes the tube closed with the resiliency of the tube re-opening it (discussed further below.)

As mentioned, the second pinch slider (150) has a second pinch surface (152) and oppositely opposed second ride surface (151). Like the first pinch slider (140), the second pinch slider (150) has two elongated slots and is mounted on support posts (144) which protrude from the right tray. The second ride surface rides on the second elongated slide surface (127) of the trigger button means (110). The second pinch slider (150) acts like a valve stem and moves back and forth as the second recess (128) in second elongated slide surface (127) passes underneath it when the trigger is displaced.

There is a second pinching back surface (156) that protrudes from the housing tray that is oppositely opposed to the second pinch surface (152). The second pinching back surface (156) is spaced apart a distance from the second pinch surface (152) such that a tube (420) that is seated, and preferably conformingly seated, between the second pinching back surface (156) and the second pinch surface (152) has a substantially open lumen when the second ride surface (151) rides in the second recess (128) and has a pinched closed lumen when the second ride surface rides (151) otherwise on the second elongated slide surface (127). In operation, the second pinch surface (152) buttresses against a second silicone tube (420). As it moves back and forth, it squeezes the tube closed with the resiliency of the tube re-opening it. (discussed further below.)

The result being, including, that with about one half displacement of the trigger button means (110) the lumen of the first tube (410) is open with the lumen of the second tube (420) being pinched closed and with an about full displacement of the trigger button means (110) the lumen of the second tube (420) is open with the lumen of the first tube (410) being pinched closed.

Returning to a discussion on the means for biasing (135), the amount of resistance provided by this means in conjunction with the force required to close silicone tubes (410, 420) should be such that it not be so great that a user will jerk the instrument or otherwise compromise control. The resistance should not be so small that the trigger feels overly soft, does not return to its extended position and/or inadvertently or unintentionally displaces as the user grasp and manipulates the instrument. Trigger resistance can be modified related to slope of ramps (see, by way of inference, Example 5). Returning to the pinching back surfaces (145, 155). While this second pinching back surface is claimed distinctly from the first pinching back surface (155), the two can be integral.

Referring to FIG. 6, another embodiment of the control system (200) utilizes a rocker-like trigger button means (210). The trigger button means (210) has a forward portion (215) that extends forward from the housing (5). This trigger button means (210) has an axis about which it rotates. At the point of this axis is hole (225). In a right tray (205), there is post (226) that protrudes perpendicular from the right tray (205). The trigger button (210) is rotatably mounted on this post (226) by reception through the hole (225).

The forward portion (215) has two finger contact surfaces (216, 217). One finger contact surface (216) is above the axis of rotation as demarcated by the hole (225) and the other finger contact surface (217) is below. There is a posterior portion (220) disposed in the handle portion (60) of the housing (5). This posterior portion (220) provides structural support and balance to the trigger button and is capable of interfacing with a biasing spring (discussed below.)

There is a means for biasing with an appropriate amount of resistance. A torsion spring is the most preferred means for biasing in this embodiment. The torsion spring is held in a preloaded state with inner surface of inner side of the right tray acting as a stop feature. In the alternative, a stop feature or shoulder can protrude from the right housing. The legs of the torsion spring contact the posterior portion of the rocker switch like trigger button (220). In another alternative, there are trigger ribs to contact the spring legs. Trigger rotation can be modified related to slope of ramps (see, Example 2.)

There is a slot (230) that is spaced apart from the axis hole (225) and spaced apart from the first contact surface (216). This slot receives a post (235) protruding from a reciprocating member (240) (discussed below) so as to form a linkage.

The reciprocating member (240) has a substantially linear slide surface (243) with two recesses (241, 242). There are two pinch cylinders (245, 246) that are seated between shoulders that protrude from the internal side of the right housing tray (205). For each pinch cylinder (245, 246), there is a pinching back surface which opposes it. These features are spaced apart such that a silicone tube (410, 420) seated between a pinch cylinder (245, 246) and the pinching back surface has an open lumen when the recess (241, 242) is under the pinching cylinder and a pinched closed lumen when the slide surface (243) is otherssie underneath it. The result being that when the rocker-like trigger button means (210) is depressed by a user into one or the other of its on positions, there is two stage valving for irrigation and suction.

Referring to FIG. 7, another embodiment of the control system (300) utilizes a dual plunger-like trigger button means (310). The trigger button means (310) has a forward portion (315) that extend forward from the housing (5). This forward portion (315) has a contact surface. The trigger button (310) has a support post (322) that extends posterior so as to be disposed in the handle portion (60) of the housing (5). This support post travels in channel formed by the lower exterior surface of shoulder (325) and upper exterior surface of shoulder (326) and thereby provides structural support for the trigger button (310) to displace longitudinally.

There is a means for biasing forward the trigger (310). This means can be a compression spring. The compression spring spans from the rear of the posterior portion of the trigger button to a shoulder protruding from the right tray. It can be a torsion spring. It can be an elastic band or member. It can be an hydraulic or air cylinder. It can be a motor powered by electricity, pressurized hydraulic fluid or compressed air. A spring is preferred and a compression spring is most preferred. This means for biasing is discussed further below.

Protruding posterior from the trigger button (310) is a first rod (320) and second rod (321). The rods (320, 321) extend in the posterior direction so as to be disposed in the body portion (60) of the housing. As explained below, the rods (320, 321) have features. In a right tray, there are two pairs of parallel shoulders (325, 326) that form a channel in which the rods (320,321) travel.

A inner lateral surface of the first rod (320) has a first recess (324). In line with this first recess (324) are openings in pairs of shoulders (325) so that a silicone tube can pass there through. There is a shelf or plate that is fastened to the tray that runs over the inner surface of the first rod and functions as a pinching back surface. A inner lateral surface of the second rod (321) has a recess. This second recess is posterior relative to the first recess (322) in the first rod (320). In line with this second recess are openings in the pair shoulders (321) so a silicone tube can pass there through. There is a shelf or plate that is fastened to the tray that runs over the inner surface of the second rod and functions as a pinching back surface. Silicone tubes are thread through the aforementioned openings in the pairs of shoulders (320, 321). As the trigger is displaced in the posterior direction, when the portion of the rod with no recess is opposite the silicone tube, the tube is closed off. When the trigger is displaced such that a recess is opposite the silicone tube, the tube is open. The result being a mode of action and valving where an about half pump of the dual plunger-like trigger button means (310) turns on irrigation or suction. An about full pump turns this off and turns on the other.

Returning to the means for biasing, it has an appropriate amount of resistance as discussed above with respect to a single plunger like means for triggering. Trigger resistance can be modified related to slope of ramps (see, Example 5.)

Another embodiment (not illustrated) of the control system is comprised of a plunger valve as described in the parent application, where one pump actuates irrigation or suction and two pumps actuates the other. In another embodiment, the trigger button means and control system are positioned on the body portion or forceps-like arms, as described in the parent application. In an alternative embodiment, there is a first valve with a trigger button means extending from the housing (5) and positioned for actuation by a user and a second valve with a trigger button means extending from the housing and positioned for actuation by a user, as more fully described in the parent application. Each valve is in intermittent fluid communication between the common conduit (30) and the fluid transmission means. The fluid communication means is in fluid communication with fluid and vacuum sources.

The irrigation-fluid and aspiration-suction control system (100, 200, 300) can be a system with a magnet, motor, hydraulic cylinder, compressed air cylinder or other mechanical assist that may be actuated by the trigger button means (110, 210 and 310). In one embodiment, there is an electrical switch, and preferably a momentary contact switch, which actuates a magnet which results in a longitudinal displacement of a bar-like structure.

Transmission Means Subcomponent

Referring to FIG. 2, there is a irrigation-fluid and aspiration-suction transmission means. One structure of this means is a pair of tubes (410, 420) which runs through the butt portion (50) and body portion (10). One tube (410 or 420) provides vacuum and the other tube provides a irrigation fluid. As discussed above, these tubes (410, 420) interact with the control system. Other structures are co-axial conduits with two channels and side-by-side conduit strips where there are two conduits/channels with one delivering fluid and the other suction.

In an embodiment of the invention, at the posterior of the butt portion (50) there can be connectors (not illustrated) for the tubing (410, 420) for attachment to vacuum and irrigation fluid sources (not illustrated.) The connectors can be a standard luer lock (a known apparatus conventionally used to connect a needle to an intravenous set.) In another embodiment, the butt portion (50) and/or body portion (10) can have a lid on the top or side to facilitate access to internal area of the instrument. In the internal area, there are connectors (ports) for the tubing (410, 420). When the lid is open, the tubes (410, 420) can be attached to or released from the connectors (ports.)

In an embodiment of the four function surgical instrument (1), a luer lock (not illustrated) on the posterior region of the butt portion (50) is connected to an appropriately sized connecting tube (410, 420)—tubing from an intravenous set—which is in turn attached to a 50 milliliter syringe containing heparin/saline. Variation of pressure applied to the syringe will produce a corresponding variation of the rate of fluid flow from the common conduit (30). The rate of fluid flow from the common conduit (30) can thus be altered at the request an operator.

In another embodiment of the four function surgical instrument (1), one or both of the tubes (410, 420) are connected to more than one syringe through a multi-channel connector.

Where more than one syringe is provided, it is possible for more than one assistant to assist with irrigating. The length of the connecting tube (410, 420) can be selected depending upon how close or far away a surgical assistant is situated from a surgeon. Commercially available dispensable intravenous sets of different lengths may be used.

In another embodiment, the fluid may be delivered to the four function surgical instrument (1) under pressure using an automated pump. The four function surgical instrument (1) may then include a valve which is used by the surgeon to control the rate of flow of fluid from or to the four function surgical instrument (1). This valve can be suitably located on the instrument and preferably on a forceps-like arm 20. It can be located off the instrument.

Suitable tubes (410, 420) are any flexible plastic tubing. The tubes should have resiliency as necessitated by the pinch valve concept, discussed above. Standard types of tubes found in Intravenous (IV) giving sets may used. Preferably, the tubes (410, 420) have an inside diameter of about 2 to about 3 millimeters. Preferably, the tubes are made out of silicone.

Wiring and Electrical

Referring to FIG. 2, the dilation tips (40) at each distal end of each of the forcep-like arms (20) are electrical conducting and communicable with electrical power (86) from an electrical power source and preferably, an actuation means for electrical power (88).

Referring to FIGS. 1 and 4, an elongated electrical conductor originates at the proximal end of the dilation tip 42 and is in electrical communication with the dilation tip 40. The elongated electrical conductor runs laterally along the forceps-like side arm. Preferably, the conductor is embedded in a channel or recess (80) in the inner surface of the forceps-like arms (20). Less preferably, the conductor can run on the inner surface of the forceps-like sidearm. Less preferable, it can be a wire.

At about the proximal end of the forceps-like arm (20), the aforementioned channel or recess (80) is terminated. Each of elongated electrical conductors in the recess or channel (80) electrically connects with a power wire; that is, a power wire emanates from the inner surface of the proximal end of each of the forceps-like arms On the front side of the body portion (20) is two hole bridge (82) positioned as a forward facing face plate. Typically, this two hole bridge (82) is located above the Y connector block (36) to which the common conduit (30) is inserted and can be integral with the Y connector block. Each of the power wires emanating from each of the forceps-like arms threads through one the holes in the two hole bridge (82).

Referring to FIG. 4, inside the housing, protruding from the right tray an elongated shoulder (84) that traverses the length of the body portion (10) and butt portion (50) of the housing (5). This elongated shoulder (84) runs approximately parallel to the upper side of the body portion (10) and the butt portion (84) and is spaced apart there from. The space between the elongated shoulder (84) runs and the upper side of the body portion (10) and the butt portion (84) creates a cavity for the power wire to run through the body portion (10) and butt portion (50 of the housing (5).

Two separate power wires can run above elongated shoulder (84) in the above described cavity with two wires exiting the instrument. In the alternative, the two separate power wires can be joined into one multi-conductor wire. This joining can occur just posterior to the two hole bridge (82). Accordingly, one wires would exit the instrument.

Referring to FIGS. 2 and 4, as discussed above, in the butt portion (50) there are on or more openings (52) for wire or wires to exit the instrument (1). Optionally, there can be a connector at the posterior side of the butt portion (50) to provide a junction for attachment and release of an electrical wires.

There is an actuation means for electrical power with one wire going through a switch to a hot side for electrical power and the other wire going to ground. Thus an electric circuit is creatable from an electric power source so that electric power is supplied for bipolar cauterization at the dilation tips (40). In a preferred embodiment of the present invention, the actuation means is a foot pedal switch (88). This foot pedal switch (88) is in electrical communication with an electric power source such that power is turned on and supplied for bipolar cauterization at the dilation tips (40). In other embodiment of the present invention, the actuation means for electrical power is a momentary contact switch, touch surface, or throw pole switch.

Embodiments for Macrosurgical Instrument and Microsurgery

The invention herein is scalable to achieve different surgical utilities. In embodiments of the invention, the instrument can be macrosized and preferably, it is macrosized about twice the size of microsized instrument. Preferably, embodiments of the invention that are a macrosized instrument are similar in outward respects to embodiments of the invention that are a microsized instruments.

Making

The housing and forceps-like arms can be made out of plastic with polycarbonate being a preferred plastic. They are manufactured by molding methodologies with injection molding being preferred. Preferably, they are manufactured in two halves; that is, a right/upper tray and a left/lower tray. The two halves are pressed together or preferably held together by screw fasteners. Embodiments of the invention as disclosed herein are suited for low production costs.

Use

The instrument is used as a clinical devise in surgery. It is ergonomical, user friendly all-in-one instrument. The instrument can have an innovative trigger mechanism that is a single poll, two stage actuator such that a half a pump of the trigger delivers irrigation or aspiration and a full pump delivers the other.

It is common in surgery for a surgeon (user) to irrigate, dissect to clean away debris, aspiration, carry out anastomosis to suture a blood vessel and at any time carry out cauterization. The user utilizes the user's first (thumb) finger and second (index) finger to manipulate the forceps-like arms (20). The user utilizes the user's third (index) finger to control the trigger button means (110, 210, 310) so as to actuate irrigation and suction. The user utilizes the user's foot to control a foot pedal switch (88) to actuate cauterization.

Embodiments of the invention are a microsurgical instrument for use in operating on small structures such as nerves and vessels. The microsurgical instrument and macro surgical instrument are for all forms of surgery and by way of example, neurosurgery, cardiac, orthopedic, autolaryngeal, maxilla-facial, obstetric, gynecology, pediatric, plastic, reconstruction and urological.

Embodiments are of the macrosurgical instrument which is an instrument about twice the size of a microsurgical instrument and similar in outward respects. The macrosurgical instrument is used, including, on operating on the abdominal cavity, bowels/intestine, a hernia and the like.

ADVANTAGES

The previously described versions of the present invention have many advantages. The instrument provides the advantages being ergonomical, being all-in-one performing the functions of dilation, irrigation, aspiration and cauterization, eliminating the need for a surgeon-user to fumble around in switching between instruments, reducing time consumption and reducing frustration.

The instrument provides the advantages of being sizable as a microinstrument and having four cooperating functions of dilation, irrigation, aspiration and cauterization. Another advantage is a mechanism for controlling irrigation-fluid and aspiration-suction that occupies a small and minimized volume such that it is containable in an instrument for microsurgery. Another advantage is that the instrument has an industrial design whose cost to manufacture is low in cost under current market conditions for medical services and therefore the instrument is economically disposable.

Another advantage is a trigger that is actuated by a user with the user's third (middle) finger allowing the user to keep the user's first finger (thumb) and second (index) finger stationary. Another advantage is that the trigger is positioned below the forceps-like arms for relatively enhanced ergonomics compared to the state of the art. Another advantage is a trigger/valve that requires relatively reduced force to actuate in the environment of achieving other advantages mentions herein. Another advantage is a short travel distance for the trigger.

Another advantage is natural and non-awkward finger positioning. Another advantage is a high level of instrument support within the hand. Another advantage is that the instrument is lightweight.

To invent a surgical instrument which provided these advantages posed many technical problems and engineering challenges for which innovation was required. One of the problems and engineering challenges was to innovate a mechanism for controlling irrigation-fluid and aspiration-suction that it occupied a small and minimized volume and could be contained in an instrument for microsurgery.

Another technical problem and engineering challenge was to innovate a mechanism for controlling irrigation-fluid and aspiration-suction that required relatively reduced force to actuate a trigger/valve in the environment of achieving the other advantages mentioned herein. Another interrelated technical problem and engineering challenge was to innovate a mechanism for controlling irrigation-fluid and aspiration-suction that was lightweight, low in cost and disposable.

A series of interrelated technical problems and engineering challenges was to innovate a design that maintained or improved the level of ergonomics as compared to the state of the art. There needed to be innovation that resulted in the following human factors being acceptable: required force on the trigger, travel distance for the trigger, finger positioning and supportable within a user's hand.

The above recitation is exemplary and not limiting.

EXAMPLES

The following examples further describe and demonstrate embodiments within the scope of the present invention. The examples are given solely for the purpose of illustration and are not to be construed as limitations or restrictions of the present invention, as persons skilled in the art will quickly realize many variations thereof are possible that are all within the spirit and scope of the invention.

Example 1

Example 1 is a proof of concept mockup of the instrument according to the present invention with a single plunger-like trigger. Referring to FIG. 5, this mock up had the principal parts, including, of a right housing, left cover, trigger, two pinch sliders, a Y-connector, a compression spring, two silicone tubes, a pipette tip and two metal tips.

Example 2

Figure 9A:
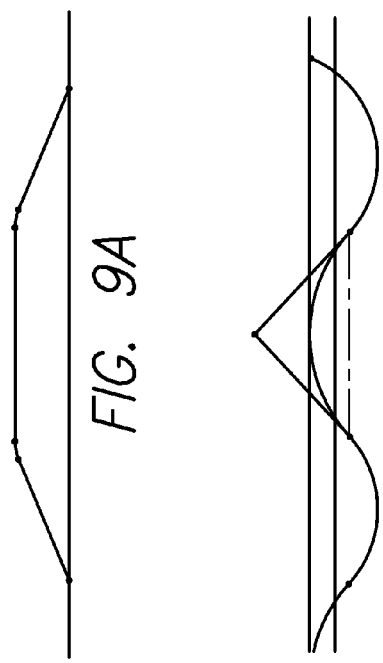
Figure 9B:
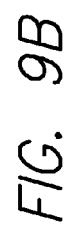

Example 2 is an analysis of operational parameters of the proof of concept mockup of Example 1 (that is, a single plunger-like trigger and illustrated in FIG. 5.) The longitudinal travel distance on the trigger was 0.4 inches. In this mockup, the finger position felt natural and the travel distance was acceptable. Referring to FIG. 9B, the initial required force on the trigger was 28 ounces. As the trigger traveled, a pinch slider slides up a recess of a elongated slide surface of the trigger and concomitantly pinching close a silicone tube. The maximum force required on the trigger was 46.4 ounces. The required force ramps at a maximum of 42.90 degrees.

Example 3

Example 3 is a proof of concept mockup of an instrument according to the present invention with a double plunger-like trigger. Referring to FIG. 7, it was constructed using silicone tubing having a 0.125 inch outside diameter by 0.063 inch inside diameter. The force to pinch close the silicone tubing with a 0.188 inch rod was 9.0 ounces. The force to pinch close the silicone tubing with a 0.128 inch rod was 7.5 ounces. The force to pinch close the silicone tubing with a 0.093 inch rod was 7.0 ounces. The compression at closure was approximately 0.045 inches.

Example 4

Example 4 is another proof of concept mockup of an instrument according to the present invention with a double plunger-like trigger. Referring to FIG. 7, it was constructed using silicone tubing having a 0.093 inch outside diameter by 0.018 inch inside diameter. The force to pinch close the silicone tubing with a 0.093 inch rod was 6.0 ounces. The compression at closure was approximately 0.060 inches.

Example 5

Example 5 is an analysis of force verses travel distance of the proof of concept mockups of Examples 3 and 4 with a double plunger-like trigger (see, illustration in FIG. 7.) Referring to FIG. 9A, the required force ramps at a maximum of 22.62 degrees.

Example 6

Example 6 is a proof of concept mockup of an instrument according to the present invention with a rocker-like trigger. Referring to FIG. 6, this mock up had the principal parts, including, of right housing, left cover, trigger and slider. A spring and pinch cylinders are internal within the housing.

Example 7

Example 7 is hypothetical example setting out a prospective utilization of an embodiment of the invention as claimed in claim 12. In a surgical procedure, as surgeon (user,) performs dilation. The dilation tips (40) are spread apart in the resting state of the instrument. Thereafter the surgeon irrigates to clean out debris. The fluid from the irrigation also serves to open the vessel. Next, the surgeon dissect to clean away debris. This dissection is followed by aspiration to suck out fluid and remove debris. Finally, the surgeon performs anastomosis to suture the blood vessel. At times during this procedure, the surgeon performs cauterization.

In this hypothetical example it is inferred and induced that the instrument would fit comfortably in the area of the web of a user's hand between a thumb and a index finger and the posterior arcuate a curly queue tail would fit around the fleshy thenar eminence of the user's palm underneath the user's thumb. It is further inferred and induced that that the instrument is more practical and ergonomically superior than prior art devises none of which are believed to have all the functions. It is further inferred and induced that the instrument provides for better gripping for more effective manipulation and greater comfort for easier and longer use without fatigue than prior art devises, none of which are believed to have all the functions.

Figure 8:
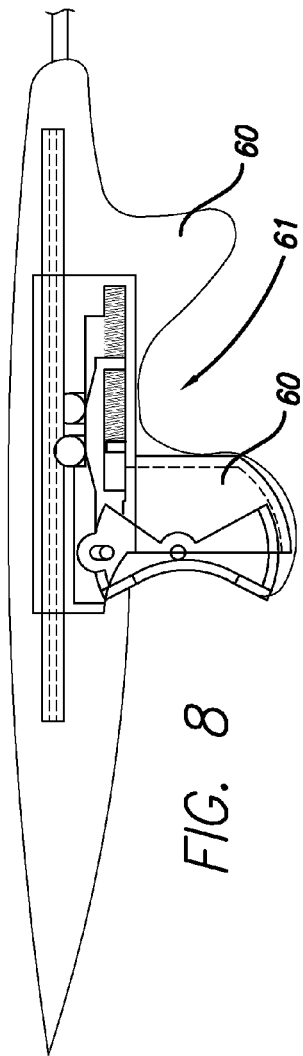
FIG. 8 which is side view of the exterior of an embodiment of the present invention looking onto a left side.

Although the present invention has been described in considerable detail with reference to certain preferred versions thereof, other versions are possible with substituted, varied and/or modified materials and steps are employed. For example, referring to FIG. 8, the handle portion (60) can have an open area (61). For another example, instead of a disposable the four function microsurgical instrument, instrument is in a modular configuration so that the instrument can be disassembled for easy cleaning and reassembled. Preferably, there is one module comprised of the forceps-like side arms with a harness or docking apparatus for reception to the central body portion. There are other units containing the other components of the instrument as previously described. These other versions do not depart from the invention. Therefore, the spirit and scope of the appended claims should not be limited to the description of the preferred versions contained herein.

What is claimed is:

1. A surgical instrument possessing the four functions of vessel dilation, irrigation, aspiration and cauterization for use by a user comprised of:
   a. a housing comprised of:
      i. a body portion having a longitudinal axis so as to define forward and posterior directions;
      ii. a handle portion that depends from the body portion and
      iii. a butt that extends from the body portion in the posterior direction;
   b. a pair of oppositely opposed forceps-like arms that extend in the forward direction from the body portion that are resiliently mounted to the body portion and insulative with each forceps-like arm having a distal end;
   c. A dilation tip at each distal end of each of the forceps-like arm that are electrical conducting and communicable with electrical power;
   d. a common conduit that extends in the forward direction from the body portion for the delivery irrigation-fluid and aspiration-suction in proximity to the dilation tips and
   e. a triggered controlled irrigation-fluid and aspiration-suction transmission system partially disposed in the housing in fluid communication with the common conduit and comprising:
   a trigger having a forward portion and a posterior portion, where said posterior portion has a first elongated slide surface which has a first recess and a second elongated slide surface that is substantially parallel to the first elongated slide surface and which has a second recess where said second recess is posterior relative to the first recess and where said trigger displaces in the posterior direction;
   a means for biasing the trigger forward;
   a first pinch slider having a first pinching back surface and an oppositely opposed first ride surface where the first ride surface rides on the first elongated slide surface;
   a second pinch slider having a second pinch surface and an oppositely opposed second ride surface where the second ride surface rides on the second elongated slide surface;
   a first pinching back surface oppositely opposed to the first pinch surface that is spaced apart a distance from the first pinch surface such that a tube seated between the first pinch surface and the first pinching back surface has a substantially open lumen when the first ride surface rides in the first recess and has a pinched closed lumen when the first ride surface rides otherwise on the first elongated slide surface;
   a second pinching back surface oppositely opposed to the second pinch surface that is spaced apart a distance from the second pinch surface such that a tube seated between the second pinch surface and the second pinching back surface has a substantially open lumen when the second ride surface rides in the second recess and has a pinched closed lumen when the second ride surface rides otherwise on the second elongated slide surface; and
   a tube seated between the first pinch surface and the first pinching back surface and a tube seated between the second pinch surface and the second pinching back surface that are connectable to a common conduit and sources for vacuum and fluid,
   whereby with about one half displacement of the rigger the lumen of the first tube is open with the lumen of the second tube pinched and with an about full displacement of the trigger the lumen of the second tube is open with the lumen of the first tube pinched.

2. The surgical instrument of claim 1 where the instrument is sized for being a microsurgical instrument.

3. The surgical instrument of claim 1 where the instrument is sized for being a macrosurgical instrument.

4. The surgical instrument of claim 1 where the handle portion has a posterior arcuate.

5. The surgical instrument of claim 1 where the forceps-like arms have at least one gripping pad.

6. The surgical instrument of claim 1 where the dilation tips are in communication with an electrical power source and a foot pedal switch for actuation.

7. A surgical instrument possessing the four functions of vessel dilation, irrigation, aspiration and cauterization for use by a user comprised of:
   a. a housing comprised of:
      i. a body portion having a longitudinal axis so as to define forward and posterior directions, a pair of oppositely opposed lateral sides, front side and an upper side;
      ii. a handle portion that depends from the body portion approximately perpendicular to the longitudinal axis of the body portion so as to define a lower direction having oppositely opposed lateral sides, a forward side, a lower side and a posterior side that has an arcuate shape so as to form a saddle which sits in the first palmar web space of the user's hand resting against the thenar eminence of the user's hand where the handle portion has a width that is suitable for grasping between the thenar eminence and a curled middle finger that rests on the finger contact surface of a single button plunger-like trigger button and iii. a butt portion that extends in the posterior direction from the body portion about along the longitudinal axis of the body portion with an upper side, oppositely opposed lateral sides, posterior side and a lower side that is restable on at least a portion of the first dorsal web space of a user's hand;

b. a pair of oppositely opposed forceps-like arms that extend in the forward direction from the body portion about along the longitudinal axis of the body portion that are resiliently mounted to the body portion and insulative with each forceps-like arm having a distal end;

c. A dilation tip at each distal end of each of the forceps-like arm that is electrically conducting and in communication with an electrical power source and an actuation means for electrical power;

d. a common conduit that extends in the forward direction from the body portion between the pair of oppositely opposed forceps-like arms about along the longitudinal axis of the body and has an end in proximity to the dilation tips;

e. a triggered controlled irrigation-fluid and aspiration-suction transmission system partially disposed in the housing that has a single button plunger-like trigger that displaces longitudinally and that extends forward from the handle portion and is positioned so as to be actuatable by the user's second finger, is in fluid communication with the common conduit, is communicable with irrigation-fluid and aspiration-suction sources whereby an about one half displacement of the single button plunger-like trigger actuates irrigation or suction and an about a full displacement of the single button plunger-like trigger actuates the other, wherein each dilation tip comprises a first length and a second length, the second length being thicker than the first length and having an inner surface for contacting a blood vessel such that the inner surface can be pressed together and still leave a gap between the respective first lengths in which at least a portion of the common conduit can reside without being constricted when the dilation tips are pressed together.

8. The surgical instrument of claim 7 where the instrument is sized for being a microsurgical instrument.

9. The surgical instrument of claim 7 where the instrument is sized for being a macrosurgical instrument.

10. The surgical instrument of claim 7 where the forceps-like arms have at least one gripping pad for receiving a user's thumb or first finger.

11. The surgical instrument of claim 7 where the actuation means for electrical power is a foot pedal switch.

12. The surgical instrument of claim 7 where:
a. the forceps-like arms have at least one gripping pad for receiving a user's thumb or first finger and
b. the actuation means for electrical power is a foot pedal switch.

13. A surgical instrument possessing the four functions of vessel dilation, irrigation, aspiration and cauterization for use by a user comprised of:

f. a housing comprised of:
iv. a body portion having a longitudinal axis so as to define forward and posterior directions;
v. a handle portion that depends from the body portion and
vi. a butt that extends from the body portion in the posterior direction;

g. a pair of oppositely opposed forceps-like arms that extend in the forward direction from the body portion that are resiliently mounted to the body portion and insulative with each forceps-like arm having a distal end;

h. A dilation tip at each distal end of each of the forceps-like arm that are electrical conducting and communicable with electrical power;

i. a common conduit that extends in the forward direction from the body portion for the delivery irrigation-fluid and aspiration-suction in proximity to the dilation tips and j. a triggered controlled irrigation-fluid and aspiration-suction transmission system partially disposed in the housing that has a trigger button means positioned for actuation by the user and is in fluid communication with the common conduit wherein each dilation tip comprises a first length and a second length, the second length being thicker than the first length and having an inner surface for contacting a blood vessel such that the inner surface can be pressed together and still leave a gap between the respective first lengths in which at least a portion of the common conduit can reside without being constricted when the dilation tips are pressed together.

14. The surgical instrument of claim 13 where the handle portion has a posterior arcuate.

15. The surgical instrument of claim 13 where the forceps-like arms have at least one gripping pad.

16. The surgical instrument of claim 13 where the dilation tips are in communication with an electrical power source and a foot pedal switch for actuation.

17. The surgical instrument of claim 13 where the triggered controlled irrigation-fluid and aspiration-suction transmission system has a trigger button means that extends forward from the handle.

18. The surgical instrument of claim 13 where the triggered controlled irrigation-fluid and aspiration-suction transmission system:
a. has a trigger button means that is a plunger-like trigger that extends forward from the handle and that displaces longitudinally and
b. is configured so that about a half a longitudinal displacement of the trigger actuates irrigation or suction and an about full longitudinal displacement of the trigger actuates the other.

19. The surgical instrument of claim 13 where:
b. the handle portion has a posterior arcuate;
c. the forceps-like arms have at least one gripping pad for receiving a user's thumb or first finger;
d. the dilation tips are in communication with an electrical power source and a foot pedal switch for actuation and
e. the triggered control led irrigation-fluid and aspiration-suction transmission system:
ii. has a trigger button means that is a plunger-like trigger that extends forward from the handle and that displaces longitudinally and
iii. is configured so that about a half a longitudinal displacement of the trigger actuates irrigation or suction and an about full longitudinal displacement of the trigger actuates the other.

* * * * *